United States Patent [19]

Fix et al.

[11] 4,440,740
[45] Apr. 3, 1984

[54] α-KETO ALDEHYDES AS ENHANCING AGENTS OF GASTRO-INTESTINAL DRUG ABSORPTION

[75] Inventors: Joseph A. Fix; Stefano A. Pogany, both of Lawrence, Kans.

[73] Assignee: Merck & Co., Inc., Rahway, N.J.

[21] Appl. No.: 371,873

[22] Filed: Apr. 26, 1982

[51] Int. Cl.³ .................... A61K 43/00; A61K 49/00; A61K 31/11
[52] U.S. Cl. ......................................... 424/1.1; 424/9; 424/333; 562/577; 568/355; 568/412
[58] Field of Search ............... 424/1, 9, 333; 562/577; 568/335, 412

Primary Examiner—Benjamin R. Padgett
Assistant Examiner—M. Moskowitz
Attorney, Agent, or Firm—Manfred Polk; Michael C. Sudol, Jr.; Mario A. Monaco

[57] ABSTRACT

A method and drug form enhancing the absorption of a rectally or orally administered drug from the rectal compartment into the blood stream of a warm blooded animal. The method includes the steps of preparing a drug form capable of being rectally and orally administered. The drug form comprises a therapeutically effective unit dosage amount of a selected drug of the type which is capable of being absorbed into the blood stream from the gastrointestinal area and an α-keto aldehyde or salts thereof being present in the drug form in a sufficient amount to be effective in enhancing the drug absorption rate, when administering the drug form to warm blooded animals.

17 Claims, No Drawings

α-KETO ALDEHYDES AS ENHANCING AGENTS OF GASTRO-INTESTINAL DRUG ABSORPTION

BACKGROUND OF THE INVENTION

Field of the Invention and Description of the Prior Art

This invention relates to a method for administering drugs to warm blooded animals by oral or rectal delivery and it particularly relates to a method for enhancing the absorption of such orally or rectally delivered drugs from the gastrointestinal tract to the blood stream.

One known method of drug administration is accomplished by the incorporation of a drug in a "suppository", which generally speaking, is a medicated solid dosage form generally intended for use in the rectum, vagina, and to a lesser extent, in the urethra. Molded rectal suppositories usually employ vehicles that melt or soften at body temperatures so that the drug may be released for use. On the other hand, soft elastic gelatin capsule suppositories rely on the presence of moisture in the rectum which causes the capsule to open and release its contents which contains its therapeutic agent. Drugs administered in suppository form are administered for either local or systemic effect. The action of the drug is dependent on the nature of the drug, its concentration, and its rate of absorption. Although rectal suppositories are commonly used for the treatment of constipation and hemorrhoids, that is, for local effect, such rectal suppositories are also administered rectally for systemic action. A wide variety of drugs may be rectally administered, as by the use of suppositories, including, for example, analgesics, antispasmodics, sedatives, tranquilizers, and antibacterial agents.

Both oral and rectal drug administration has many advantages over other routes of drug administration, such as parenteral or topical administration. For example, many drug substances that are given parenterally have restricted use in that they are usually given in hospital or clinical settings.

Oral and rectal drug administration also have advantages over parenteral administration. For example, oral or rectal drug administration does not require highly trained personnel required for parenteral administration and also represents significantly less hazard to the patient, such as possible antigenicity development with certain drugs (e.g., hormones).

Also surface active agents have been used to increase gastrointestinal drug absorption, especially from the rectal compartment, although tissue damage is a significant concern. In view of the known disadvantages of parenteral drug administration, drug administration by oral or rectal route enables many drugs to be absorbed from the anorectal area and yet retain their therapeutic value. The lower hemorrhoidal vein, surrounding the colon and rectum, enters the inferior vena cava and thereby bypasses the liver. Therefore, drugs are absorbed directly into the general circulation when rectally administered.

SUMMARY OF THE INVENTION

The primary use of our invention is to provide a means of promoting significant gastrointestinal absorption of water-soluble drugs which are poorly absorbed from conventional formulations.

It is therefore an important object of the present invention to provide a unique method for enhancing the absorption of orally and rectally administered drugs from the gastrointestinal area to the blood stream.

It is also an object of the present invention to provide an improved rectal suppository drug form which enhances the absorption of rectally delivered drugs contained in a soft elastic gelatin capsule or a molded suppository.

It is a further important object of the present invention to provide an improved method for oral or rectal administration of drugs wherein enhanced absorption results from the incorporation of α-keto aldehydes or salts thereof into the drug formulation.

It is a still further object of this invention to provide a stable drug form utilizing enhancing agents or adjuvants which when administered orally or rectally will provide increased blood levels of the drug or therapeutic agent.

Further purposes and objects of this invention will appear as the specification proceeds.

The foregoing objects are accomplished by providing a method and drug form wherein the absorption of orally and rectally administered drugs into the bloodstream of warm blooded animals is enhanced, the method comprising the steps of preparing a drug form capable of being orally or rectally administered, the drug form comprising an effective unit dosage amount of a drug of a type which is capable of being absorbed from the gastrointestinal compartment into the blood stream, and α-keto aldehydes or salts thereof, the α-keto aldehyde or salts thereof being present in said drug form in an amount sufficient to be effective in enhancing the absorption of a drug into the blood stream from the gastrointestinal compartment, and thereafter orally or rectally administering the drug form to a warm blooded animal.

DETAILED DESCRIPTION OF THE PREFERRED EMBODIMENTS

The present invention, generally, comprises the steps of preparing a drug form capable of being orally or rectally administered, wherein the drug form comprises an effective unit dosage amount of a drug capable of being absorbed into the blood stream of a warm blooded animal from the gastrointestinal compartment and α-keto aldehydes or salts thereof being present in the drug form in a sufficient amount to be effective in enhancing the absorption rate, and orally or rectally administering the drug form to the warm blooded animal.

Our method for enhancing the absorption of drugs from the gastrointestinal compartment is useful for a wide range of drugs or drug categories including, but not limited to β-lactam antibiotics such as penicillin, including penicillin G., penicillin V., ampicillin, amoxicillin, methacillin, carbenicillin, ticaricillin and cephalosporins, such as cephalosporin C, cefazolin, cefoxitin, cephamandole, cefuroxine, cephapirin, cephaloridine, cephmetazole, cephanone and oxacephalosporin, all of which drugs are capable of being absorbed into the blood stream of a patient from the gastrointestinal compartment. Other drug catagories include xanthines, anticancer agents, other antibiotics (such as erythromycin, thienamycin and derivatives thereof such as N-formimidoyl thienamycin and gentamicin), antiarrythmics, polypeptides, cardiovascular agents, antidiabetics, antiulcers, antifungals, antinauseants, sedatives, diuretics, antihypertensives, antiinflammatories, anticoagulents, antihelminthics, antiviral agents, radioopaques and radio-nuclide diagnostic agents, polynucleotides and drugs for the treatment of Parkinsons disease. Still other specific drugs useful in the method and in combination with the hereinafter described adjuvants are hereinafter identified, particularly in Example 3. The amount of the drug used in our method for enhancing drug absorption varies over a wide range, generally any therapeutically effective unit dosage amount of the selected drug is used.

The compounds that are used as absorption enhancers or adjuvants in our method and in our composition are known generally as α-keto aldehydes and have the following formula:

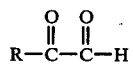

$$R-\overset{\overset{O}{\|}}{C}-\overset{\overset{O}{\|}}{C}-H \qquad (I)$$

wherein R is hydroxy, phenyl, substituted phenyl, or loweralkyl ($C_{1-5}$) and wherein the substituents on the substituted phenyl radical can be halo, loweralkyl ($C_{1-5}$), or hydroxy and the pharmaceutically acceptable acid addition salts thereof when R is hydroxy.

Preferred α-keto aldehydes are those of Formula I and the pharmaceutically acceptable acid addition salts thereof wherein R is hydroxy, phenyl or methyl.

Typical α-keto aldehydes of Formula I which can be combined with the drugs mentioned in this invention are:
glyoxylic acid or the pharmaceutically acceptable acid addition salts thereof,
phenyl glyoxal or
methyl glyoxal.

The term "pharmaceutically acceptable acid addition salt" as used herein generally includes the nontoxic acid addition salts of the α-keto aldehyde compounds of formula (I), formed with nontoxic inorganic or organic acids. For example, the salts include those derived from inorganic acids such as hydrochloric, hydrobromic and the like; and the salts prepared from organic acids such as acetic, stearic, tartaric, maleic and the like. These salts and their preparation from the parent α-keto aldehyde compounds are well known by those skilled in this art.

As in the case of the drugs used in our method and drug form, the amount of absorption enhancer or adjuvant used may vary over a wide range; in general, the identity and the amount of the adjuvant used in connection with the drug are selected in order to be effective in enhancing the absorption of the drug from the gastrointestinal compartment into the bloodstream.

Generally the amount of adjuvant in our drug forms is from 10–500 mg in each unit dose. The percentage of drug in the total combination of drug plus adjuvant is 5–50% with a preferred percentage of a drug in the total combination of adjuvant plus drug being 5–30%.

The particular method used for the oral or rectal administration of the drug and the adjuvant is preferably by use of the appropriate size, shape or form of any of the various types of drug delivery devices known to the pharmaceutical art. Thus, for rectal delivery, the drug and adjuvant may be administered by suppositories or alternatively, the drug may be administered with the adjuvants by means of a microenema. Useful rectal suppositories with which the present method may be used include cocoa butter suppositories, synthetic fat suppositories, and gelatin capsules including soft elastic gelatin cpsule type suppositories as well as other controlled release devices such as an osmotic pump or other polymeric devices.

A preferred form of suppository comprises a soft elastic gelatin capsule having an outer shell which encloses the drug and the adjuvant in a suitable vehicle which will not attack the walls of the seamless gelatin capsule. The shell encapsulates a preselected drug form and the adjuvant. The gelatin capsule shell may be formulated in accordance with conventional techniques for making filled, seamless, soft elastic gelatin capsules containing therapeutically effective unit dosage amounts of the active drug ingredient. For example, one conventional shell formulation includes about 30–53 parts by weight of gelatin, 15–48 parts by weight of a plasticizer, such as glycerine or sorbitol, and about 16–40 parts by weight of water. Additionally, the gelatin shell may contain preservatives such as mixed parabens, ordinarily methyl or propyl parabens in about a 4:1 ratio. The parabens may be incorporated in the shell formulation in minor proportions as compared to the total weight of the shell formulation. Conventional gelatin capsules utilize gelatin having a bloom value of about 160–200 although this amount may be varied.

In a conventional manner, the gelatin composition is mixed and melted under vacuum conditions. The capsules may be simultaneously formed and filled using a conventional method and apparatus. The gelatin capsules are formed into a desired shape and size for insertion into the rectal compartment. It is to be understood, however, that the particular method used for making the soft elastic gelatin shell and for incorporating the fill therein are not considered part of the invention herein.

The drug forms of this invention which are suitably administered in oral dosage form, such as by tablet or capsule, are done so by combining the active drug in a therapeutic amount and the α-keto aldehyde or salt thereof in a sufficient quantity to be effective to enhance oral delivery with an oral pharmaceutically acceptable inert carrier, such as lactose, starch (pharmaceutical grade), dicalcium phosphate, calcium sulfate, Kaolin, mannitol and powdered sugar. In addition, when required, suitable binders, lubricants, disintegrating agents, and coloring agents can also be added. Typical binders include, without limitation, starch, gelatin, sugars such as sucrose, molasses, and lactose, natural and synthetic gums, such as acacia, sodium alginate, extract of Irish moss, carboxymethylcellulose, methylcellulose, and polyvihnylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose and wood products, alginic acid, guar gum, citris pulp, carboxymethylcellulose, and sodium lauryl sulfate. Optionally, if desired, a conventionally, pharmaceutically acceptable dye can be incorporated into the oral dosage unit form, e.g., any of the standard FD & C dyes.

One of the more important uses of our method and drug form for oral or rectal administration of drugs is in the administration of sustained release or programmed release drug forms which will slowly release the drug substances into the gastrointestinal compartment of a warm blooded animal.

The following data sets forth specific experiments illustrating various embodiments of the present invention.

EXAMPLE 1

Aqueous microenemas were administered to rats at an intrarectal depth of 2.5 cm containing 10 mg/kg target drug and 20 mg/kg α-keto aldehyde absorption enhancer. Serum samples were collected and drug bioavailability determined versus intravenous administration of the target compound. Glyoxylic acid, methylglyoxal and phenylglyoxal were tested as representative compounds in the α-keto aldehyde series. Data has been oriented for rectal delivery of two antibiotics (shown below).

| α-Keto aldehyde | % Bioavailability* | |
| --- | --- | --- |
| | Sodium Cefoxitin | Gentamicin Sulfate |
| Glyoxylic acid | 16 ± 7.6 | 55 ± 10.1 |
| Phenylglyoxal | 38 ± 7.6 | 67 ± 9.3 |
| Methylglyoxal | 20 ± 1.8 | 47 ± 8.5 |

*Control formulations, without α-keto aldehyde adjuvants, resulted in 5% bioavailability with both sodium cefoxitin and gentamicin sulfate. The results are the mean ± S.D. for 3 animals per experiment.

EXAMPLE 2

Effect of methylglyoxal and phenylglyoxal on rectal absorption of Ara-C, 4-Amino-1β-D-Arabinofuranosyl-2(1H)-pyrimidinone (Cytarabine), an antineoplastic, antiviral agent

| Adjuvant | Area under plasma curve | 90 min** 0 min | % Bioavailability of Ara-C |
| --- | --- | --- | --- |
| None | 75 ± 19.4 | | 13.1 |
| 2% Methylglyoxal | 574 ± 100.2 | (P 0.01) | 50.7 |
| 2% Phenylglyoxal | 798 ± 71.0 | (p 0.001) | 70.5 |

Ara-C present at 1% w/v concentration
**μg min/ml (micrograms per minute per ml)

EXAMPLE 2A

Effect of Phenylglyoxal on Rectal and Duodenal Absorption of a Cyclic Hexapeptide Somatostatin Analog Specifically
Cyclo-(N-Me-Ala-Tyr-D-Trp-Lys-Val-Phe)

| Route | Concentration of Phenylglyoxal (mg/ml) | Percent Bioavailability |
| --- | --- | --- |
| Rectal | 0 | 7 |
| | 25 | 34 |
| Duodenal | 0 | 1 |
| | 25 | 20 |

Rat Model:
250 μl volume, pH 5/animal
0.4 mg
Cyclo-(N—Me—Ala—Tyr—D-Trp—Lys—Val—Phe)
microenema - 250 μl at 2.5 cm intrarectal depth
duodenal - 250 μl injection 1 cm distal to pylorus

EXAMPLE 3

Following the procedure of Example 1 or 2 but using an appropriate amount of the following drugs in place of gentamicin sulfate, sodium cefoxitin, or Ara-C used in Example 1 the corresponding drug/adjuvant mixture is produced.

β-Lactam antibiotics

1. Ampicillin
2. Amoxicillin
3. Methacillin
4. Cephapirin
5. Cefalothin
6. (6R-cis)-3-[[(Aminocarbonyl oxy]methyl]-7-methoxy-8-oxo-7-[(2-thienylacetyl))amino]-5-thia-1-azabicyclo-[4.2.0]oct-2-ene-2-carboxylic acid (cefoxitin);
7. Carbenicillin
8. Penicillin G
9. Ticaricillin
10. Cefazolin
11. Cephaloglycin
12. Cephaloridine
13. Cephalosporin C
14. Cephmetazole
15. Oxacephalosporin
16. Penicillin V
17. N-formimidoyl thienamycin monohydrate
18. Cephalexin
19. Carbenicillin
20. Cephmandole

Other antibiotics

Erythromycin
Thienamycin and derivatives thereof
N-formimidoyl thienamycin monohydrate
(6R-cis)-3-[[Aminocarbonyloxy]methyl]-7-methoxy-8-oxo-7-[(2-thienylacetyl))amino]-5-thia-1-azabicyclo-[4.2.0]oct-2-ene-2-carboxylic acid (cefoxitin)
1-ethyl-6-fluoro-1,4-dihydro-4-oxo-7-(1-piperazinyl)-3-quinolinecarboxylic acid
3-fluoro-D-alanine and D-4-(1-methyl-3-oxo-1-butenylamino)-3-isoxazolidinone sodium salt hemihydrate
7-[(hydroxyphenylacetyl)amino]-3-[[(1-methyl-1H-tetrazol-5-yl)thio]methyol]-8-oxo-5-thia-1-azabicyclo-[4.2.0]oct-2-ene-2-carboxylic acid (cephamandole)
1-ethyl-1,4-dihydro-7-methyl-4-oxo-1,8-naphthyridine-3-carboxylic acid (nalidixic acid)
6-[[amino(4-hydroxyphenyl)acetyl]-amino]-3,3-dimethyl-7-oxo-4-thia-1-azabicyclo-[3.2.0]heptane-2-carboxylic acid (amoxicillin)
gentamycin

Xanthines 3,7-Dihydro-1,3-dimethyl-1H-purine-2,6-dione (theophylline)

Anticancer agents

Allopurinol
Viscristine
Vinblastine
Methotrexate
Dactinomycin

Antiarrhythmics 2-(Diethylamino)-N-(2,6-dimethyl-phenyl)acetamide (lidocaine)
Procainamide
Quinidine sulfate

| Polypeptides | |
| --- | --- |
| Insulin | Oxytocin FSH |
| Stomatostatin and analogues | Endorphin Substance P. |
| Calcitonin | Enkephalin |
| Pentagastrin | Growth Hormone |
| Gastrin | Prolactin |
| | Cyclic Hexapeptide Somatostatin Analogs |

Cardiovascular agents

Antidiabetics

Insulin
Chlorpropamide
Tolazamide

Antiulcers

Cimetidine

Antifungals

Griseofulvin
Amphotericin B
Miconazole

Antinauseants

Sedatives 3-(5H-dibenzo[a,d]cyclohepten-5-ylidene)-N,N-dimethyl-1-propanamine (cyclobenzaprine)
α-[2-[4-[(4-chlorophenyl)phenylmethyl]-1-piperazinyl]ethoxyethanol (hydroxyzine)
7-chloro-1,3-dihydro-1-methyl-5-phenyl-2H-1,4-benzodiazepin-2-one (diazepam)
7-chloro-N-methyl-5-phenyl-3H-1,4-benzodiazepin-2-amine 4-oxide (chlorodiazepoxide)
4-[4-(4-chlorophenyl)-4-hydroxy-1-piperidinyl]-1-(4-fluorophenyl)-1-butanone (haloperidol)
Glutethimide Diuretics 3,5-diamino-N-(aminoimino-methyl)-6-chloropyrazinecarboxamide (amiloride)
6-chloro-3,4-dihydro-2H-1,2,4-benzothiadiazine-7-sulfonamide-1,1-dioxide (hydrochlorothiazide)
amiloride hydrochloride and hydrochlorothiazide (moduretic)
(6,7-dichloro-2-methyl-2-phenyl-1-oxo-5-indanyloxy)-acetic acid Antihypertensives S-(−)-1-(tert-butylamino)-3-[(4-morpholino-1,2,5-thiadiazol-3-yl)oxy]-2-propanol (timolol)
N-[(S)-1-(ethoxycarbonyl)-3-phenylpropyl]-L-alanyl-L-proline maleate
5-(aminosulfonyl)-4-chloro-2-[(2-furanylmethyl)amino]-benzoic acid (furosemide)
Clonidine
1-[(2S)-3-mercapto-2-methylpropionyl]-L-proline (captopril)

Drugs for the treatment of Parkinsons disease

S-α-hydrozino-3,4-dihydroxy-α-methylbenzenepropanoic acid monohydrate (carbidopa)
carbidopa and 3-hydroxy-L-tyrosine (levodopa) (Sinemet)
3-hydroxy-L-tyrosine (levodopa), (L-Dopa)
Benzotropine mesylate Anti-inflammatory 2',4'-difluoro-4-hydroxy-[1,1'-biphenyl]-3-carboxylic acid (diflunisal)
1-(p-chlorobenzoyl)-5-methoxy-2-methylindole-3-acetic acid (indomethacin)
(Z)-5-fluoro-2-methyl-1-[[4-(methylsulfinyl)phenyl]methylene]-1H-indene-3-acetic acid (sulindac)
α-methyl-4-(2-methylpropyl)benzeneacetic acid (ibuprofen)
(+)-6-methoxy-α-methyl-2-naphthaleneacetic acid (Naproxen)
5-(4-chlorobenzoyl)-1,4-dimethyl-1H-pyrrole-2-acetic acid (Zomepirac)
4-butyl-1,2-diphenyl-3,5-pyrazolidinedione (phenylbutazone)
9-fluoro-11β,17,21-trihydroxy-16a-methylpregna-1,4-diene-3,20-dione (dexamethasone)
11β,17,21-trihydroxypregna-1,4-diene-3,20-dione (prednisolone)

Antihelminthics

Ivermectin
Chloroquine

Antiviral agents

Ara-A-9-(β-Arabinofuranosyl)adenine
Ara-C-4-Amino-1β-D-Arabinofuranosyl-2-(1H)-pyrimidinone
Acycloguanosine
Amantadine hydrochloride Radio-opaques and radio-nuclide diagnostic agents Polynucleotides (−)-1-(cyclopropylmethyl)-4-[3-(trifluoromethylthio)-5H-dibenzo(a,d)cyclohepten-5-ylidene]piperidine hydrochloride
(+)10,11-dihydro-5-methyl-5H-dibenzo[a,d]cyclohepten-5,10-imine oxalate
L-N-(2-oxopiperidin-6-yl-carbonyl)-histidyl-L-thiazolidine-4-carboxamide While in the foregoing there has been provided a detailed description of particular embodiments of the present invention, it is to be understood that all equivalents obvious to those having skill in the art are to be included within the scope of the invention as claimed.

What we claim and desire to secure by Letters Patent is:

1. A method for enhancing the absorption of an orally or rectally administered drug from the gastrointestinal compartment into the bloodstream, said method comprising the steps of preparing a drug form capable of being orally or rectally administered, said drug form comprising a therapeutically effective dosage amount of a drug capable of being absorbed into the bloodstream from the gastrointestinal compartment said drug comprising antibiotics, xanthines, anticancer agents, polypeptides, antiarthritic, cardiovascular agents, antidiabetics, antiulcers, antifungals, antinauseants, sedatives, diuretics, antihypertensives, anti-inflammatories, anthelmintics, antiviral agents, radio-opaques and radionuclide diagnostic agents, polynucleotides, or anti-Parkison agents and an α-keto aldehyde of the formula:

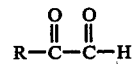

wherein R is hydroxy, phenyl, substituted phenyl or lower alkyl ($C_{1-5}$) and wherein the substituents on the substituted phenyl radical can be halo, lower alkyl, ($C_{1-5}$) or hydroxy and the pharmaceutically acceptable acid addition salts when R is hydroxy or a pharmaceutically acceptable salt thereof as adjuvants, said adjuvant being present in said drug in a sufficient amount to be effective in enhancing said absorption and the percentage of the drug to drug plus adjuvant is 5% to 50% by weight and administering said drug form into said gastrointestinal compartment.

2. The method of claim 1 wherein the drug comprises an antibiotic.

3. The method of claim 1 wherein said adjuvant comprises an α-keto aldehyde comprising glyoxylic acid, phenylglyoxal or methylglyoxal or a pharmaceutically acceptable acid addition salt thereof.

4. The method of claim 1 wherein said drug comprises amiloride, hydrochlorothiazide, amiloride and hydrochlorothiazide, carbidopa, levodopa, cefoxitin, cefmetzole, cyclobenzaprine, diflunisal, iodomethacin, sulindac, timolol, (−)-1-(cyclopropylmethyl)4-[3-(trifluoromethylthio)-5H-dibenzo(a,d)-cyclohepten-5-ylidene]-piperidine hydrochloride, N-[(S)-1-(ethoxycarbonyl)-3-phenylpropyl]-L-alanyl-L-proline maleate, (+)10,11-dihydro-5-methyl-5H-dibenzo[a,d]cyclohepten-5,10-imine oxalate, 1-ethyl-6-fluoro-1,4-dihydro-4-oxo-7-(1-piperazinyl)-3-quinoline-carboxylic acid, 3-fluoro-D-alanine and D-4(1-methyl-3-oxo-1-butenylamino)-3-isoxazolidinone sodium salt hemihydrate, L-N-(2-oxo-piperidin-6-ylcarbonyl)-histidyl-L-thiazolidine-4-carboxamide, N-formimidoyl thienamycin monohydrate, (6,7-dichloro-2-methyl-2-phenyl-1-oxo-5-indanyloxy) acetic acid, ibuprofen, naproxen, 5-(4-chlorobenzoyl)-1,4-dimethyl-1H-pyrrole-2-acetic acid, phenylbutazone, dexamethasone, prednisolone, clonidine, propranolol, diazepam, chlordiazepoxide, furosemide, cephamandole, nalidixic acid, amoxicillin, haloperidol, captopril or Ara-C.

5. The method of claim 1 wherein said drug comprises cefoxitin.

6. The method of claim 1 wherein said drug comprises gentamycin.

7. The method of claim 1 wherein said drug comprises 4-amino-1B-D-arabinofuranosyl-2-(1H)-pyrimidinone.

8. The method of claim 1 wherein said adjuvant comprises:
glyoxylic acid or a pharmaceutically acceptable acid addition salt thereof,
phenyl glyoxal or
methyl glyoxal.

9. A rectally or orally administered drug form comprising a therapeutically effective dosage amount of a drug capable of being absorbed into the bloodstream from the gastrointestinal compartment said drug comprising an antibiotic, xanthine, anticancer agent, polypeptide, antiarthritic, cardiovascular agent, antidiabetic, antiulcer, antifungal, antinauseant, sedative, diuretic, antihypertensive, anti-inflammatory, anthelmintic, antiviral agent, radio-opaque and radionuclide diagnostic agent, polynucleotide, or an anti-Parkison agent and an α-keto aldehyde of the formula:

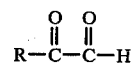

wherein R is hydroxy, lower alkyl ($C_{1-5}$), phenyl, or substituted phenyl wherein the substituents are halo, lower alkyl ($C_{1-5}$), hydroxy or a pharmaceutically acceptable acid addition salt thereof as adjuvant, said adjuvant being present in said drug form in a sufficient amount to be effective in enhancing the absorption of said drug from said gastrointestinal compartment into the bloodstream and wherein the percentage of drug to drug plus adjuvant is 5% to 50% by weight.

10. The drug form of claim 9 wherein said adjuvant comprises: glyoxylic acid or a pharmaceutically acceptable acid addition salt thereof, phenylglyoxal or methylglyoxal.

11. The drug form of claim 9 wherein said drug comprises amiloride, hydrochlorothiazide, amiloride and hydrochlorothiazide, carbidopa, levodopa, cefoxitin, cefmetzole, cyclobenzaprine, diflunisal, indomethacin, sulindac, timolol, (−)-1-(cyclopropylmethyl) 4-[3-(trifluoromethylthio)5H-dibenzo(a,d)cyclohepten-5-ylidene]-piperidine hydrochloride, N-[(S)-1-(ethoxycarbonyl)-3-phenylpropyl]-L-alanyl-L-proline maleate, (+)10,11-dihydro-5-methyl-5H-dibenzo[a,d]cyclohepten-5,10-imine oxalate, 1-ethyl-6-fluoro-1,4-dihydro-4-oxo-7-(1-piperazinyl)-3-quinoline-carboxylic acid, 3-fluoro-D-alanine and D-4-(1-methyl-3-oxo-1-butenylamino)-3-isoxazolidinone sodium salt hemihydrate, L-N-(2-oxopiperidin-6-ylcarbonyl)-histidyl-L-thiazolidine-4-carboxamide, N-formimidoyl thienamycin monohydrate, (6,7-dichloro-2-methyl-2-phenyl-1-oxo-5-indanyloxy)acetic acid, ibuprofen, naproxen, 5-(4-chlorobenzoyl)-1,4-dimethyl-1H-pyrrole-2-acetic acid, phenylbutazone, dexamethasone, prednisolone, clonidine, propranolol, diazepam, chlordiazepoxide, furosemide, cephamandole, nalidixic acid, amoxicillin, haloperidol, captopril or 4-amino-1β-D-arabinofuranosyl-2-(1H)-pyrimidnone.

12. The drug form of claim 9 wherein said drug comprises cefoxitin.

13. The drug form of claim 9 wherein said drug comprises gentamycin.

14. The drug form of claim 9 wherein said drug comprises 4-amino-1β-D-arabinofuranosyl-2-(1H)-pyrimidinone.

15. The drug form of claim 9 wherein said adjuvant comprises:
glyoxylic acid or a pharmaceutically acceptable acid addition salt thereof,
phenyl glyoxal or
methyl glyoxal.

16. The method of claim 1 wherein said drug comprises Cyclo-(N-Me-Ala-Tyr-D-Trp-Lys-Val-Phe).

17. The drug form of claim 9 wherein said drug comprises Cyclo-(N-Me-Ala-Tyr-D-Trp-Lys-Val-Phe).

* * * * *